United States Patent
Kraemer et al.

(10) Patent No.: US 7,541,001 B2
(45) Date of Patent: Jun. 2, 2009

(54) AUTOMATIC PIPETTING AND ANALYZING DEVICE

(75) Inventors: Wolfgang Kraemer, Jena (DE); Frank Tempel, Jena (DE); Thomas Moore, Jena (DE)

(73) Assignee: CyBio AG, Jena (DE)

( * ) Notice: Subject to any disclaimer, the term of this patent is extended or adjusted under 35 U.S.C. 154(b) by 639 days.

(21) Appl. No.: 11/285,965

(22) Filed: Nov. 23, 2005

(65) Prior Publication Data

US 2006/0110287 A1    May 25, 2006

(30) Foreign Application Priority Data

Nov. 24, 2004    (DE) .................... 10 2004 057 450

(51) Int. Cl.
*B01L 3/02* (2006.01)
(52) U.S. Cl. .................... 422/65; 422/63; 422/100; 422/104; 422/929; 73/864.24; 73/864.25
(58) Field of Classification Search .................. 73/1.74, 73/863.32, 864.1–864.31; 422/63, 65, 100, 422/104, 922–929
See application file for complete search history.

(56) References Cited

U.S. PATENT DOCUMENTS

| | | | |
|---|---|---|---|
| 3,772,154 A | 11/1973 | Isenberg et al. | |
| 5,443,790 A | 8/1995 | Coeurrveille et al. | |
| 6,267,927 B1 | 7/2001 | Pomar Longedo et al. | |
| 6,589,483 B1 * | 7/2003 | Maeda | 422/100 |
| 2003/0027345 A1 * | 2/2003 | Friswell et al. | 436/49 |

FOREIGN PATENT DOCUMENTS

| | | |
|---|---|---|
| DE | 197 12 195 | 9/1998 |
| DE | 198 23 222 | 12/2000 |
| DE | 100 58 237 | 5/2002 |
| EP | 0 088 679 | 9/1983 |
| EP | 0 259 386 | 4/1991 |
| EP | 0 703 455 | 3/1996 |
| EP | 1 366 822 | 12/2003 |
| JP | 6-194315 | 7/1994 |
| WO | 2004/037157 | 5/2004 |

* cited by examiner

*Primary Examiner*—Tony G Soohoo
*Assistant Examiner*—Shogo Sasaki
(74) *Attorney, Agent, or Firm*—Reed Smith LLP (57) ABSTRACT

An automatic pipetting and analyzing device for the preparation and analysis of samples in the wells of a microtitration plate has a work platform on which positioning areas for auxiliary devices and a movement area for the sample plate are provided, a passive mechanical table without its own drive unit, the sample plate lying within the inner passive slide of the passive mechanical table, and an active mechanical table which is arranged above the passive mechanical table and by which a pipetting head can be moved in X-Y direction over the work platform in order to extract, transport and dispense liquids by at least one pipetting channel and in order to displace the sample plate by a coupling connection with the inner passive slide, for example, to place the sample plate in an incubator or to position it with the individual wells in an analysis device.

9 Claims, 12 Drawing Sheets

Fig. 9 ized from EP 0 259 386 B1. b) Description of the Relevant Art Up to the present time, there is no compact, economical laboratory equipment known from practice which makes it is possible to automatically prepare samples and analyze the prepared samples. Although there are known technical solutions for this purpose such as those described in the references cited in the following, they have presumably not been realized in practice because they are either not flexible enough or are not economical.

AUTOMATIC PIPETTING AND ANALYZING DEVICE

CROSS-REFERENCE TO RELATED APPLICATIONS

This application claims priority of German Application No. 10 2004 057 450.2, filed Nov. 24, 2004, the complete disclosure of which is hereby incorporated by reference.

BACKGROUND OF THE INVENTION a) Field of the Invention

The invention is directed to a pipetting and analyzing device such as is known generically from EP 0 259 386 B1.

b) Description of the Relevant Art

Up to the present time, there is no compact, economical laboratory equipment known from practice which makes it is possible to automatically prepare samples and analyze the prepared samples. Although there are known technical solutions for this purpose such as those described in the references cited in the following, they have presumably not been realized in practice because they are either not flexible enough or are not economical.

EP 0 259 386 B1 describes a photometric analyzing device which, in contrast to the state of the art in 1986, allowed a completely monitored analyzing process from preparation of samples to evaluation of the results of photometric measurements. This analyzing device disclosed in EP 0 259 386 B1 comprises:
- a primary rack for holding a large number of sample tubes
- a mechanical table which holds a microtitration plate and is arranged alongside the primary rack and which can be positioned in any desired X-Y direction in a lower horizontal plane
- a sample distributor arm which is arranged above the primary rack and mechanical table and which can be positioned in any desired manner in an upper horizontal plane
- a photometer which is arranged within the positioning area of the mechanical table and whose beam path vertically pierces the X-Y plane of the mechanical table, and a programmable computer for controlling the entire photometric analyzing device.

The sample distributor arm advantageously has a vertically movable single-channel pipette and the device can additionally comprise an incubator or a rinse liquid trough.

U.S. Pat. No. 5,443,790 discloses an analysis device for samples which, like the device described in EP 0 259 386 B1, allows the preparation of the samples to be analyzed in reaction vessels (reaction carriers in EP 0 259 386; wells of a microtitration plate in U.S. Pat. No. 5,443,790), a thermal regulation of the samples located in the reaction vessels and the analysis of the samples through photometric measurement.

In order to prepare the samples, the required liquids which are provided in vessels supplied for this purpose on the work platform are added to and removed from the reaction vessels in predetermined amounts and in a given sequence. For this purpose, the reaction vessels are located in a defined position on the work platform of the respective device. A pipetting head (sample distributor arm in EP 0 259 386, head in U.S. Pat. No. 5,443,790) located above the work platform is driven in a horizontal plane in X-Y direction above the work platform.

In order to regulate the temperature of the samples and for analysis, the reaction vessels which are positioned on an X-Y mechanical table in EP 0 259 386 and which are embodied in practice by the wells of a microtitration plate are moved into an incubator or into the beam path of a photometer. It is apparent that this mechanical table has its own drive unit and its own control.

In contrast, the reaction vessels in the apparatus described in U.S. Pat. No. 5,443,790 remain in their defined rigid position also for the purpose of regulating temperature and analysis on the work platform.

The reaction vessels can remain in this position for regulating temperature because they are held immersed in a reservoir (bath) filled with a liquid whose temperature can be regulated. Insofar as the reaction vessels must be adjusted to different temperatures during the preparation process, this type of stationary arrangement of the reaction vessels is disadvantageous because the temperature of the reaction vessels and of the contained samples can only change slowly due to the high heat capacity of the liquid in the bath and because they must remain in the bath. It is always possible to adjust the temperature more rapidly by inserting into and removing from a preheated incubator.

The reaction vessels can also remain in their defined rigid position for analyzing the samples because provision is made for removing the sample to be analyzed from the respective reaction vessel and moving it to a vessel arranged in the beam path of the photometer, namely in this case over an opening in the working plane. Accordingly, aside from the vertical translatory movement (Z-direction) that is always necessary, the entire movement process of the device described in U.S. Pat. No. 5,443,790 is realized solely through the horizontal translatory movement of the pipetting head in the X-Y direction. Therefore, the design of the device is simpler because only the pipetting head need be driven and controlled. It must be assumed that the vessels for the samples to be analyzed are exchanged manually.

This solution has the decisive disadvantage that the sample to be analyzed must be transferred by pipetting. The limited applicability of the device to samples (reagent products) that are actually liquid is also disadvantageous.

OBJECT AND SUMMARY OF THE INVENTION

It is the primary object of the invention to provide an automatic pipetting and analyzing device which can be used flexibly and by which samples can be prepared and analyzed in a microtitration plate in a fully automated manner and which is outfitted with only one drive for generating all necessary movements in the X-Y direction.

This object is met for an automatic pipetting and analyzing device for the preparation and analysis of samples in the wells of a microtitration plate, with a work platform on which a free movement area for the microtitration plate and positioning areas for auxiliary devices such as supply vessels, a rinsing device, an incubator, and tip magazines are provided for preparing the samples, a mechanical table which can be positioned in X-Y direction in any manner in a lower horizontal plane over the work platform and which has a holder for the sample plate, a pipetting head which can be positioned in X-Y direction in any manner in an upper horizontal plane by means of a drive unit and which has at least one pipetting channel with a slip-on body for tips that can be lowered in Z-direction, wherein a coupling pin is provided at the pipetting head and a cutout which is shaped as the inverse of the coupling pin is provided at the inner passive slide, and the coupling pin and the cutout can be joined together to form a coupling connection by which a driving force acting on the pipetting head in X-Y direction is transmitted to the inner passive slide.

The invention will be described in more detail in the following with reference to an embodiment example shown in the drawings.

DESCRIPTION OF THE PREFERRED EMBODIMENTS

Figure 1:
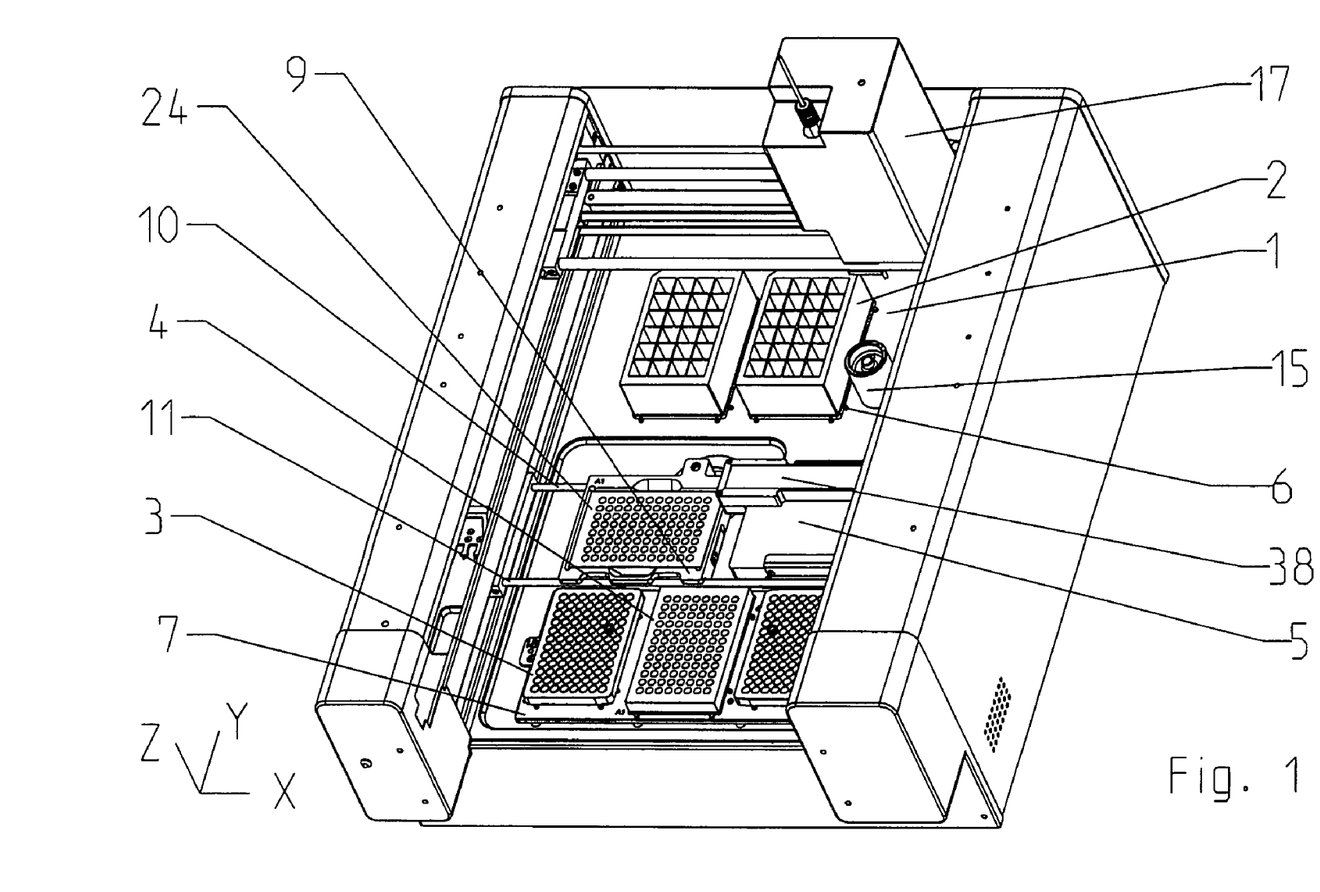
FIG. 1 is a perspective view of a device according to the invention without cover.
Figure 2:
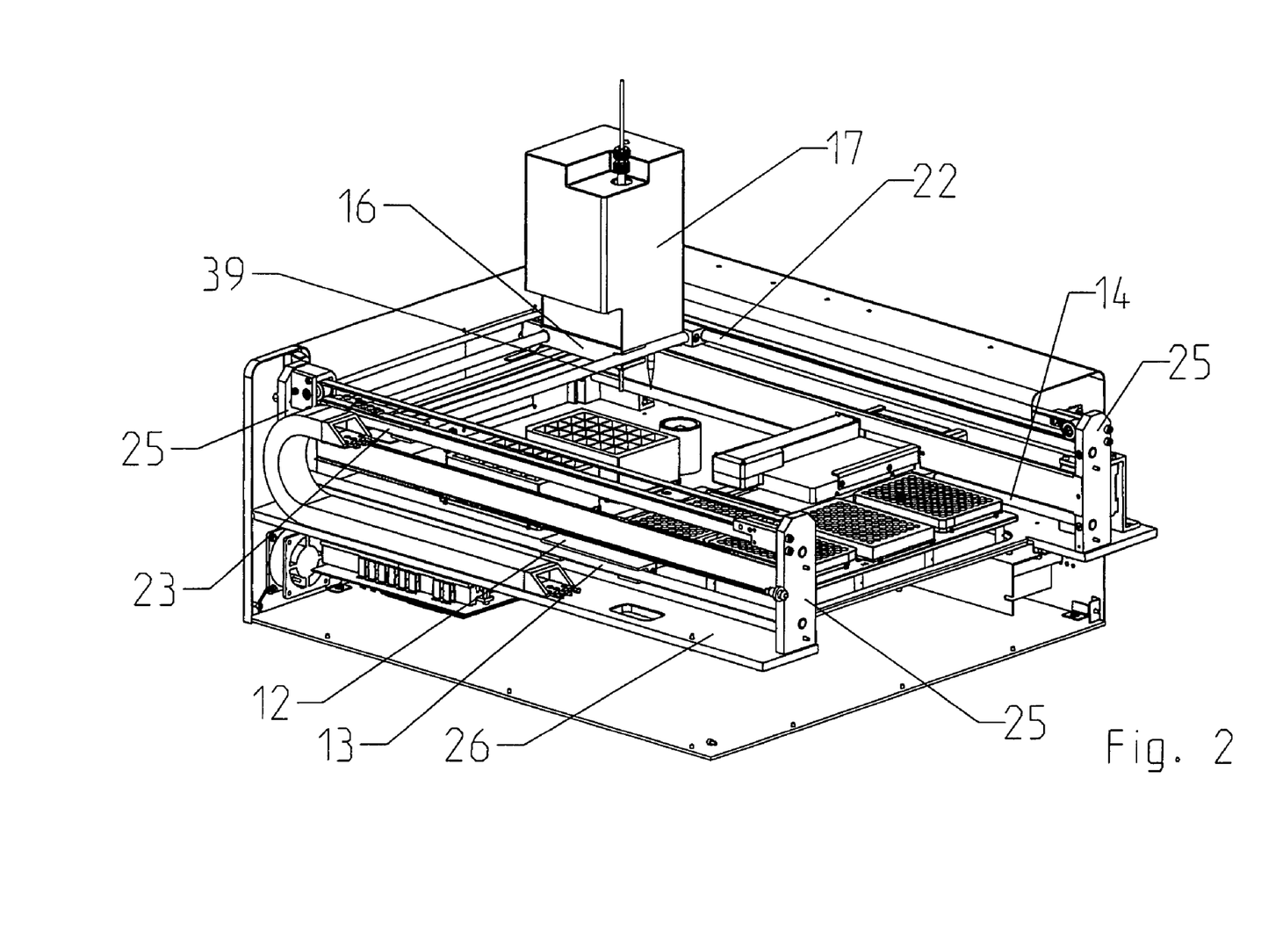
FIG. 2 shows the device according to FIG. 1 with the casing partially removed.

FIG. 1 shows a device according to the invention without the cover that usually closes the device. The drawing showing the device in the opened state allows the interior of the device to be seen, particularly the work platform 1 on which are provided positioning areas in which are arranged auxiliary devices that are necessary for the automatic operating sequence of the device. Usually, auxiliary devices of this kind are supply vessels 2, tip magazines 3, additional microtitration plates 4 containing the material to be examined, an incubator 5, or a rinsing device 15. Other auxiliary devices used for analysis can be magnetic holders for magnetic particle handling or devices for carrying out vacuum extraction steps.

In the device construction shown herein, two positioning areas are provided directly on the work platform 1 for deep well blocks serving as supply vessels 2. Deep well vessels of this kind make it possible to reserve different amounts of various liquids with relatively small block heights and, therefore, relatively shallow depths of the individual chambers (deep wells). Compared to loaded tip magazines 3 or additional microtitration plates 4, the deep well blocks have the greatest height and are therefore placed directly on the work platform 1 between positioning pins 6. An additional microtitration plate 4 contains the material to be analyzed. Only liquids are removed from this plate without carryover (by constantly changing tips) and transferred to the sample plate 24 by pipetting. The sample plate 24 is the plate in which all other reaction steps are carried out. In this way, the material in the additional microtitration plates 4 which is to be analyzed can be made available for other possible examinations in its original state.

A rinsing device 15, which is equivalent to a fountain with respect to its manner of operation, is arranged next to the supply vessels 2. In operation, rinsing liquid is pumped through an opening in a central raised portion, runs into a surrounding trough and is pumped out from the latter via an outlet. The rinsing device 15 serves to clean a suction pipe 39 by which liquids to be removed from the sample plate 24 can be disposed of more quickly and directly compared with a pipette. During the wash process, the end of the suction pipe 39 is immersed in the central raised portion and the wash liquid flows around the outer surfaces of the suction pipe 39 and cleans them. This suction pipe 39 can also be cleaned on the inside by sucking up the wash liquid.

Further, the device construction shown in the drawing shows two positioning areas for tip magazines 3 and a positioning area for an additional microtitration plate 4 over an adapter plate 7 directly on the work platform 1. At least the two positioning areas for the tip magazines 3 are cut out from the adapter plate 7 so that the tips 8, not shown here, which are suspended in the tip magazines 3 can project through.

Another positioning area is provided for an incubator 5 which is permanently installed in contrast to the other above-mentioned auxiliary devices for sample preparation. The positioning area for the incubator 5 overlaps the free movement area of a first mechanical table, designated hereinafter as passive mechanical table, which is movable over the work platform 1 in X-Y direction in a lower horizontal plane. The passive mechanical table will be described later.

An optical analysis device is provided in the free movement area of the passive mechanical table so that the prepared samples, for whose preparation the above-mentioned auxiliary devices are provided, can finally also be analyzed with this device. The type of analysis device employed is not relevant to the essence of the invention.

Basically, the analysis device comprises an illumination device 38, a transparent cover plate 35 (for transmitted light variants and incident light variants from below; the cover plate 35 is not needed for incident light variants from above) that is recessed into the work platform 1, the sample to be analyzed being positioned above this cover plate 35, and a reception device.

Depending on whether the analysis device operates by incident light methods or transmitted light methods, the illumination device 38 and the reception device are located above or below the work platform 1 or above and below the work platform 1 at a distance from the latter, which allows optimal illumination and optimal analysis of a sample that is positioned above the work platform 1 and, therefore, as the case may be, above the cover plate 35.

In the present embodiment example, the illumination device 38 is arranged above the work platform 1 (see FIG. 10) and the reception device is arranged below the cover plate 35 and, therefore, below the work platform 1.

The analysis device can be, e.g., a photometer, a spectrometer, a fluorometer, a luminometer, a turbidimeter, or a scintillation measurement arrangement.

The device can also be outfitted with non-optical analysis devices, e.g., pH value probes, contacts for sensing electrically conductive structures, or a conductimeter, which are provided in the movement area of the passive mechanical table.

It is essential to the invention that every sample to be analyzed can be positioned over the cover plate 35 by the individual drive unit for the pipetting head 17. In the same way, the samples can be positioned in the incubator 5 or relative to any non-optical analysis devices that may be provided.

The passive mechanical table mentioned above (FIG. 4 and FIG. 3b) comprises an inner passive slide 9 that can be guided in X-direction via a through-hole along one of its longitudinal sides on a first guide rod 10. A first auxiliary rod 11 engages in a groove provided on the opposite longitudinal side of the inner passive slide 9 in order to prevent the rotation of the inner passive slide 9 relative to the first guide rod 10.

The first guide rod 10 and the first auxiliary rod 11, together with the end pieces 12 which are fastened to the rod ends and fix the latter in position relative to one another, form an outer passive slide 18.

In conformity to the principle of a slide guide on round rods, one of the two end pieces 12 in this instance also has a through-hole, while a groove is arranged in the other end piece 12 (see FIG. 4).

Figure 3A:
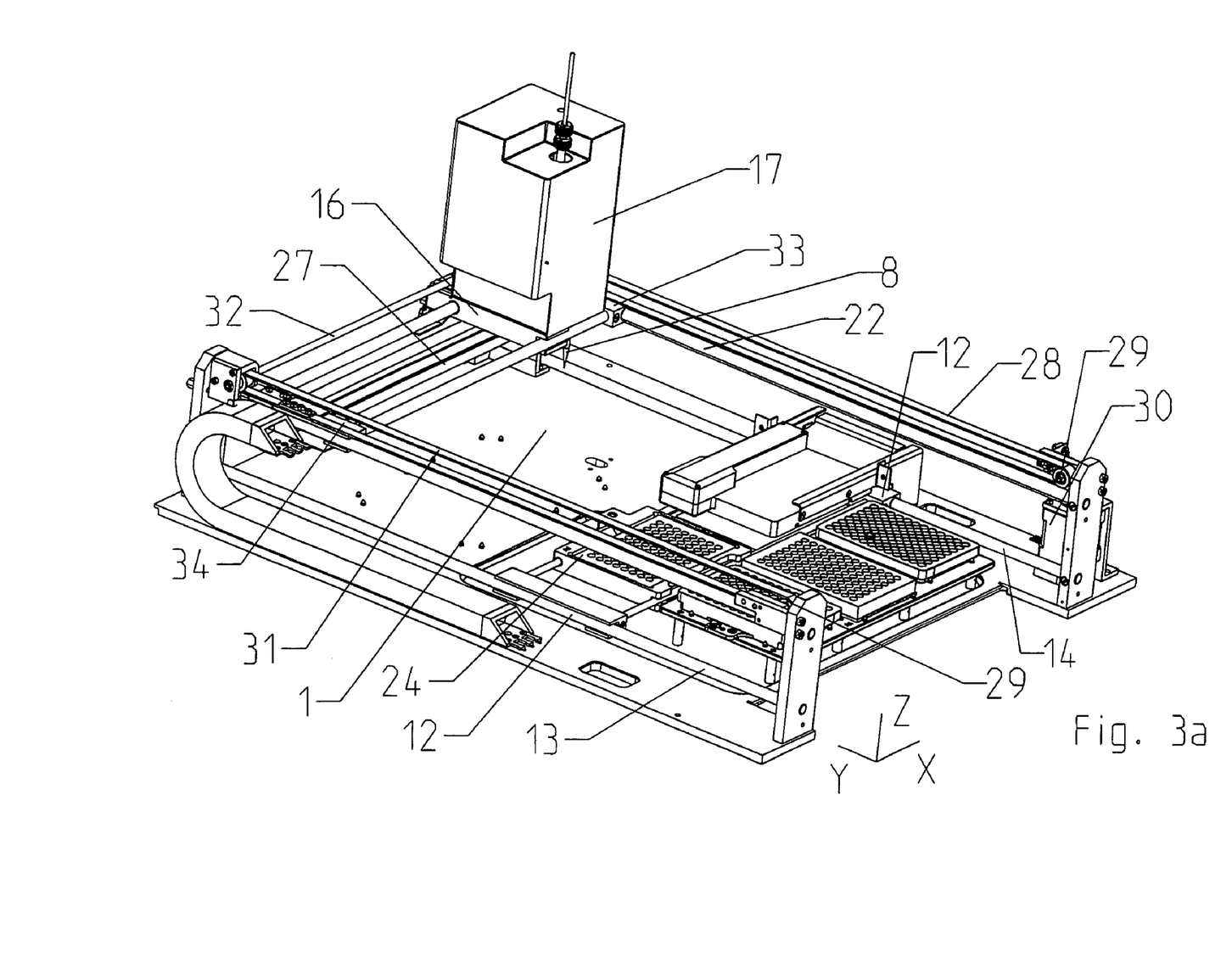
FIGS. 3a-b are two different views of the device according to FIG. 1 with the casing completely removed.
Figure 3B:
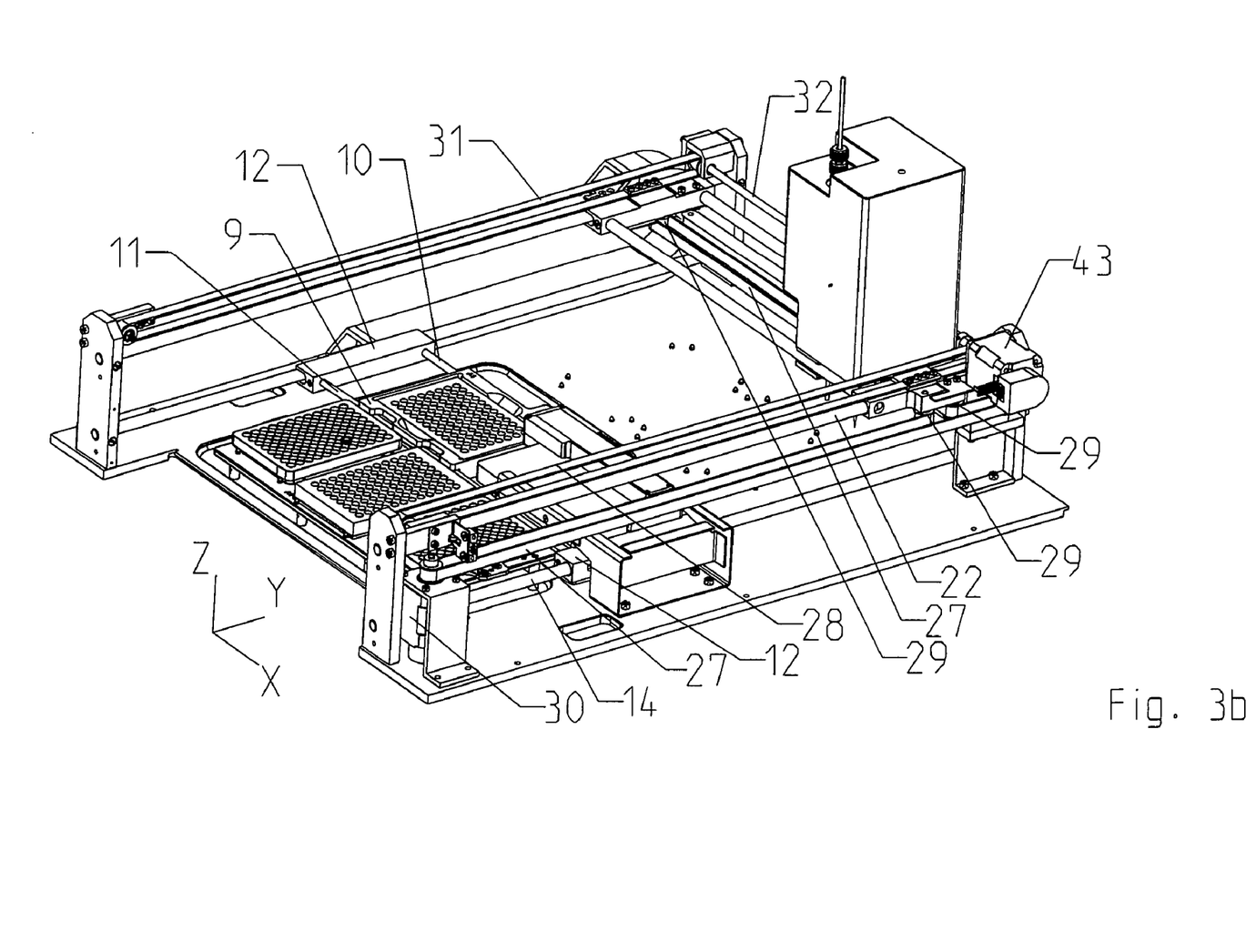
Figure 4:
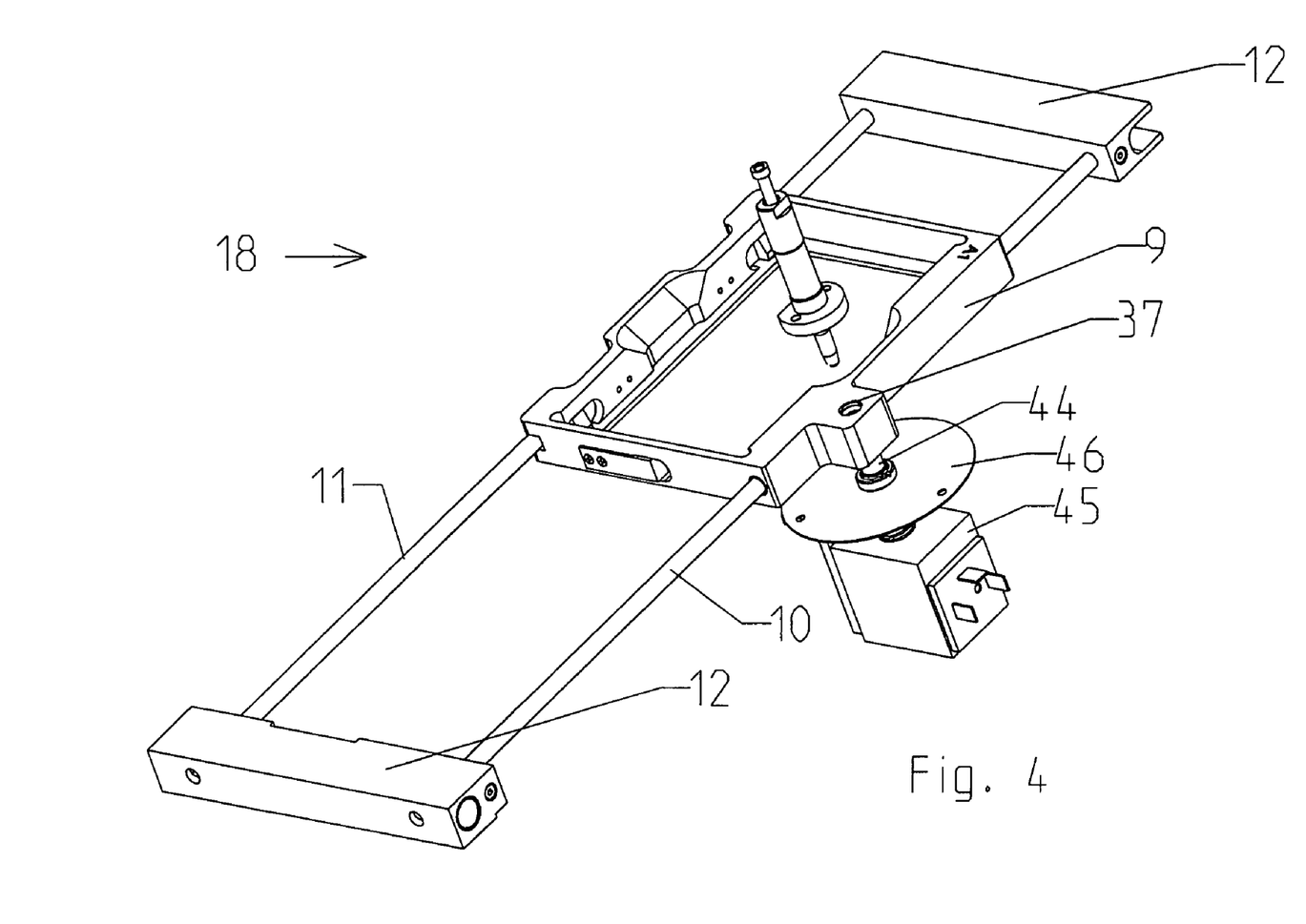
FIG. 4 shows a passive slide subassembly of a device according to FIG. 1.

As can be seen in FIGS. 3a and 3b, the end piece 12 with the groove is displaceable on a second auxiliary rod 13. The end piece 12 with the through-hole is displaceable on a second guide rod 14. Together, the described subassemblies and individual parts, starting with the inner passive slide 9, form the passive mechanical table. This passive mechanical table has the distinction that it does not have its own drive, i.e., no additional motors, transmission gear units or control devices are required for it.

According to the invention, the passive mechanical table is driven by introducing an external movement which will be explained at greater length later on.

Figure 5:
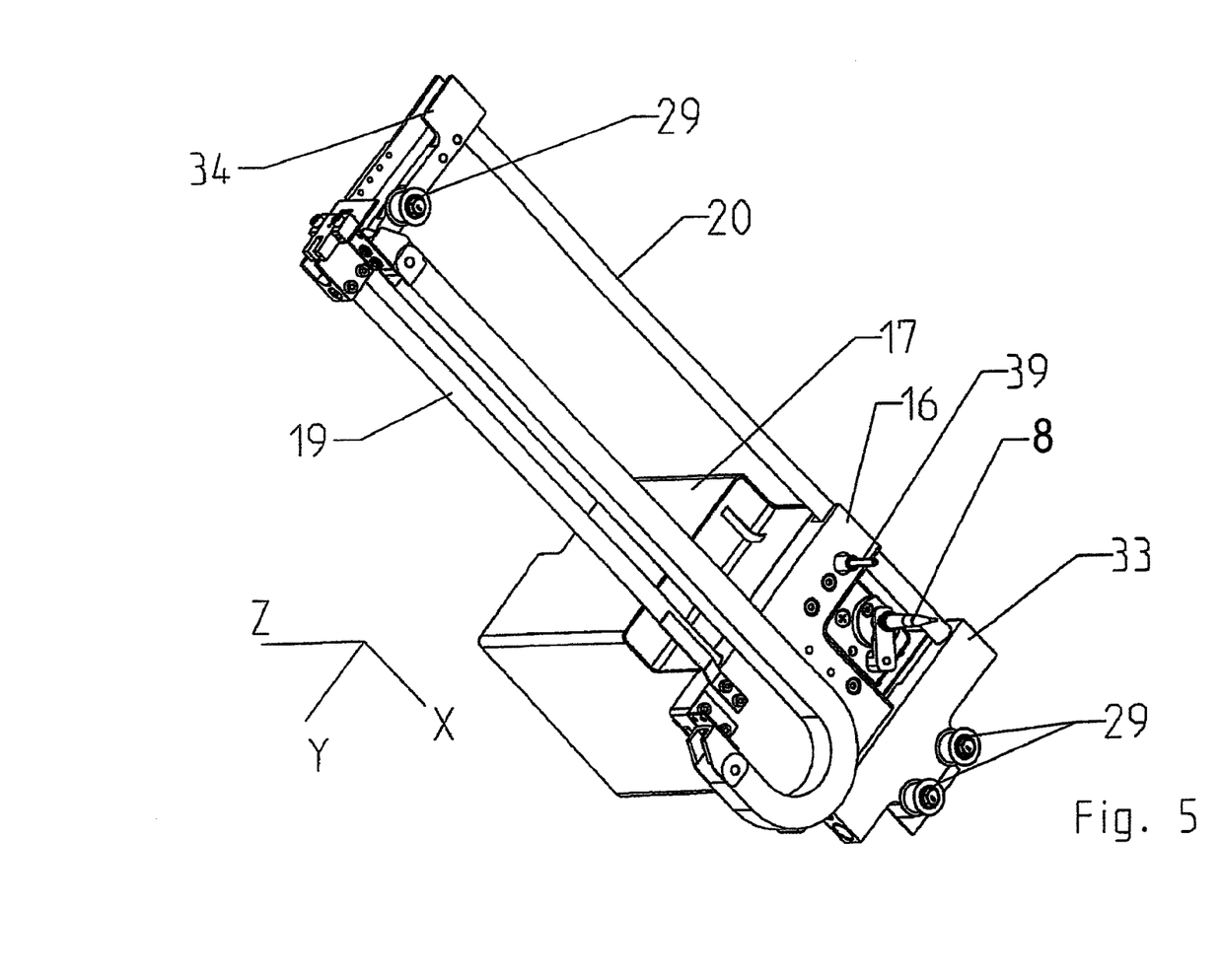
FIG. 5 shows an active slide subassembly, including pipetting head, in a device according to FIG. 1.

A second mechanical table (hereinafter: active mechanical table) which is constructed in the same way as the passive mechanical table described above is arranged in a second horizontal plane above the passive mechanical table. A pipetting head 17 is placed on an inner active slide 16 (see FIG. 5 and FIG. 3a). The inner active slide 16 is guided in X-direction in the same manner as the inner passive slide 9 on a third guide rod 19 and a third auxiliary rod 20 within an outer active slide 21. The outer active slide 21 is guided in Y-direction, similar to the outer passive slide 18, on a fourth guide rod 22 by a terminating piece 33 and on a fourth auxiliary piece 23 by an end part 34.

The positions of a microtitration plate (hereinafter: sample plate 24) that is inserted in the inner passive slide 9 (holder), in particular the position of the individual wells (depressions) and the position of the pipetting head 17 fastened to the inner active slide 16, in particular the position of the tip 8 located thereon or the position of a suction pipe 39 located thereon, can be referenced to the same Cartesian coordinate system and, therefore, to an identical neutral position.

This common coordinate system is determined by the guide rods 22, 14 and auxiliary rods 13, 23 oriented in identical direction. By selecting identical lengths for the rods for guiding the inner slides 9, 16 and the outer slides 18, 21 and the arrangement thereof in a vertical plane, respectively, both mechanical tables have the same movement area insofar as no auxiliary devices restricting the movement area are arranged on the work platform 1.

The auxiliary rods 13, 23 and the guide rods 22, 14 for guiding the outer slides 18, 21 are fixedly connected, respectively, to a frame plate 26 by two common end plates 25. This subassembly comprising guide rods with end pieces has a sufficient stability due to the two rods by which the end plates 25 are connected to one another without needing an additional connection for stiffening the subassembly.

The active mechanical table and, therefore, the movement of the pipetting head 17 are driven actively. The drive unit of the active mechanical table comprises two motors, two transmission gear units having two toothed belts 27, 28, deflecting rollers 29, and a computer-assisted control unit.

A first motor 30, shown in FIG. 3b, drives a closed first toothed belt 27 by means of a driven pinion gear, not shown. The first toothed belt 27 runs parallel to and at the height of the fourth guide rod 22 and is guided, by means of deflecting rollers 29 arranged at the outer active slide 21, along the outer active slide 21, where it is fastened to the inner active slide 16 in order to drive the pipetting head 17 fastened thereto in X-direction.

A second motor 43 drives the pipetting head 17 in Y-direction in that it drives a second toothed belt 28 by a driven pinion gear. Toothed belt 28 likewise runs parallel to the fourth guide rod 22, but so as to be rotated by 90°, and is fastened to the terminating piece 33 of the outer active slide 21. In order that the outer active slide 21 is guided exactly in the guide in spite of friction and play, the movement is transmitted by a transmission shaft 32 to a third toothed belt 31 which is fastened to the end part 34 located opposite to the terminating piece 33.

In the described embodiment example, the pipetting head 17 is a single-channel pipetting head which, as is known to the person skilled in the art, has a pump chamber in which a liquid can be received or dispensed by generating a negative or positive pressure. The liquid is received and dispensed by a pipette tip (hereinafter: tip 8) which fits on a slip-on body 36 which is symmetric with respect to rotation. The slip-on body 36 is advantageously conical.

This slip-on body 36 is particularly important to the invention. It will be clear to the person skilled in the art that this slip-on body 36 which carries a tip 8 for pipetting must be movable in Z-direction in order to move into and out of vessels for receiving or dispensing liquids and, accordingly, a drive is provided in the pipetting head 17 to bring about this movement.

The lift of the pump chamber, i.e., the possible movement range in Z-direction, and the height of the deepest vessel are adapted to one another. In the described embodiment example, the neutral position for the free end of the tip in Z-direction is just above the positioned supply vessel 2 and the lowest end position at the height of the inner surface of the bottom of the supply vessel 2. The neutral position is selected at this location so that the pump chamber with the tip 8 is moved upward when the device is initialized. In this way, the pipetting head 17 can be moved within the permissible movement space without collisions. The sample plate 24, the additional microtitration plate 4, and the tip magazines 3 are positioned at a height in Z-direction within this movement area.

In the same way as in devices of this type known from the prior art, a tip 8 mounted on the slip-on body 36 can be positioned at any position above the work platform 1 by the continuous movement of the pipetting head 17 in X-Y direction in order to receive liquid from the respective vessel or dispense liquid into the vessel after being lowered over the vessel bottom in a defined manner. In particular, the liquid is dispensed into the sample plate 24 in which the sample to be analyzed is prepared.

It is likewise known that new tips suspended in the tip magazine 3 in a defined hole arrangement can be slipped on to the slip-on body 36 by lowering in a defined manner.

Before a new tip 8 can be slipped on, the used tip 8 is stripped off by a discarding mechanism provided at the pipetting head 17 above a waste container (not shown here) which is placed directly in front of the slip-on body 36 (see FIG. 1) of the device. For this purpose, the pump chamber with the tip 8 still attached is lifted higher than the neutral position. In so doing, the tip 8 is pressed against a stop and stripped off from the slip-on body 36. The guide rods and auxiliary rods project correspondingly farther beyond the work platform 1 so that the pipetting head 17 can also be moved over the waste container located outside the work platform 1.

After the tip 8 is discarded, the pipetting head 17 moves over a tip magazine 3, positions the slip-on body 36, which is now free, exactly above the tip 8, and lowers the slip-on body 36 into the tip 8. The diameter and the angle of taper of the slip-on body 36 are adapted to the inner shape of the tip 8 in the upper edge area so that the tip 8 can be slipped onto the slip-on body 36 easily. The outer shape of the upper edge area is defined by a cylindrical collar. The upper edge surface of the collar is located in the same plane as the inlet opening of the tip 3. The discarding mechanism engages at this upper edge surface to eject the tip 8. The tip 8 is suspended in the tip magazine by the lower edge area of the collar so that the tip magazine 3 acts as a counter-support by means of the collar when the tip 8 is slipped on.

According to the invention, the slip-on body 36, in addition to holding the tips 8, has a coupling function, i.e., it also serves as one half of a coupling on the drive side and represents a coupling pin.

The half of the coupling on the driven side is formed by a cutout 37 in the inner passive slide 9, which cutout 37 is adapted to the shape and size of the slip-on body 36 and is symmetric with respect to rotation. It will be clear to the person skilled in the art that the shape of the cutout 37 is correspondingly adapted when the slip-on body 36 is cylindrical, for example, rather than conical. At least the slip-on body 36 or the cutout 37 is advantageously conical. An O-ring 48 is advantageously inserted into the cutout 37 in order to protect the surface of the slip-on body from mechanical damage and to prevent play in the coupling connection.

When the slip-on body 36 is lowered into, i.e., engages in, the cutout 37, a coupling connection is produced by means of which the force for moving the pipetting head 17 in X-Y direction is transmitted to the inner passive slide 9, and therefore to the sample plate 24, in a 1:1 ratio.

Due to the fact that the sample plate 24 can be displaced by a cross slide guide having the same dimensions as the cross slide guide of the pipetting head 17 and that the two are arranged so as to occupy the same space one above the other, the inner passive slide 9, in theory, can follow all of the movements of the pipetting head 17 in the X-Y direction when the work platform 1 is free of auxiliary devices.

Figure 6:
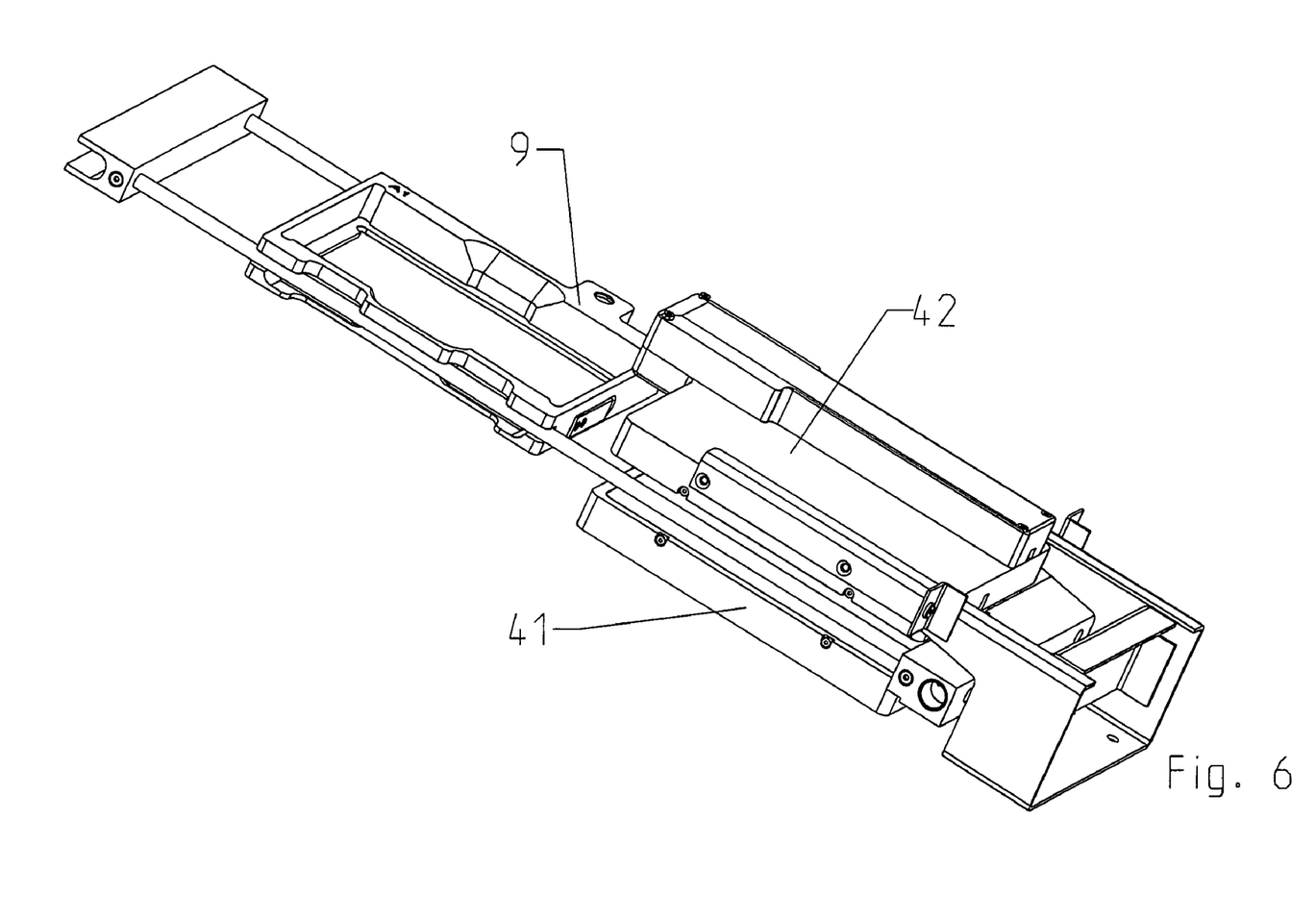
FIG. 6 shows a passive slide subassembly with incubator in a device according to FIG. 1.
Figure 7:
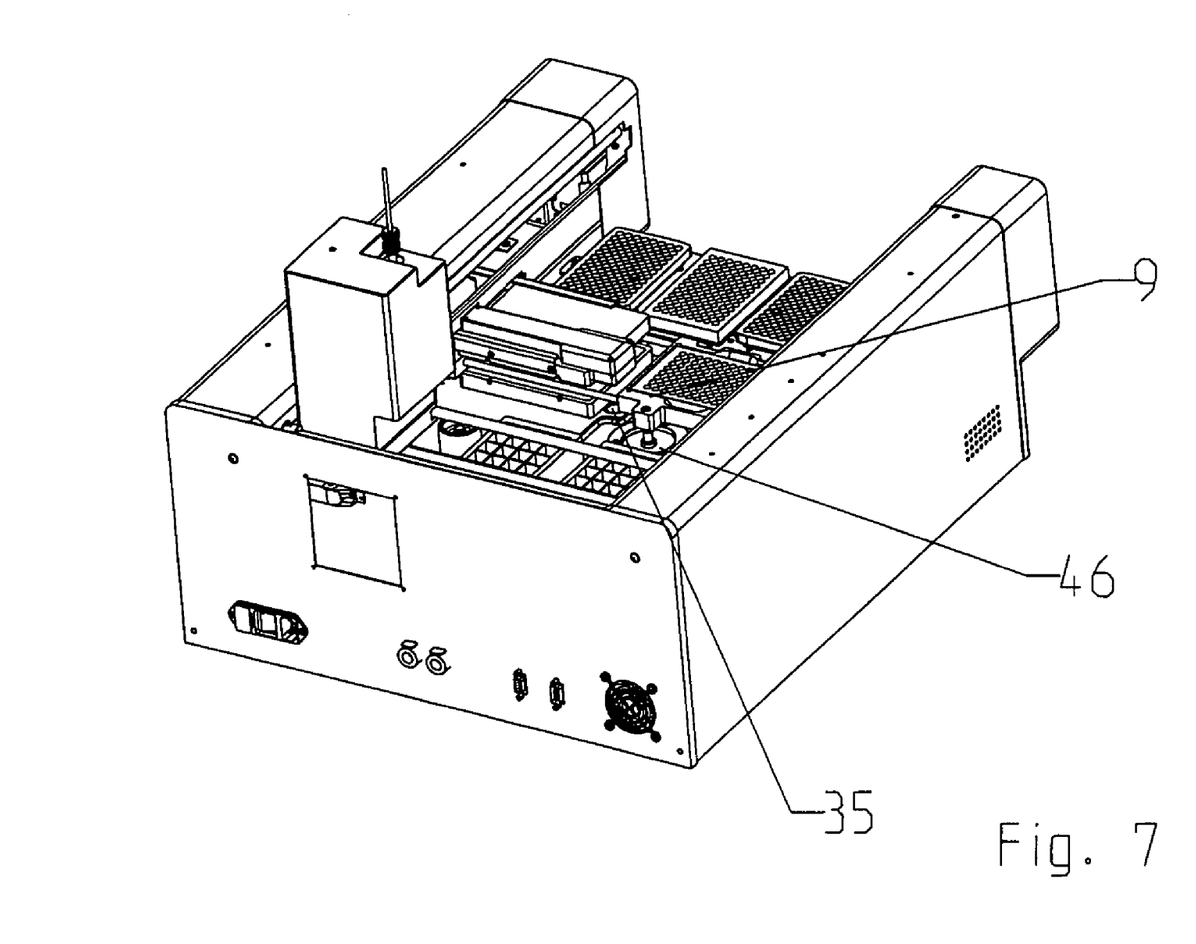
FIG. 7 is a perspective top view of a device according to FIG. 1.

Accordingly, the sample plate 24 lying in the passive slide 9 can be pushed into a specially prepared incubator 5 (see FIG. 6).

The incubator 5 comprises a lower heating plate 41 and an upper heating plate 42 between which the sample plate 24 is to be inserted. The walls of the inner passive slide 9 form the insulation for the sample plate 24 in the incubator 5 at the sides. When the inner passive slide 9 is located in the incubator 5, the incubator 5 is a closed system apart from tiny slots affording the possibility of movement to the inner and outer passive slides 9, 18.

The temperature of the upper heating plate 42 must be slighter higher than the temperature of the lower heating plate 41 so that no condensation forms on the upper heating plate 42.

In case very short incubation periods are necessary, the lower heating plate 41 can be outfitted with a lifting mechanism which presses the lower heating plate 41 against the underside of the sample plate 24 so that heat can be introduced by conduction as well as convection.

The heating plates 41, 42 are constructed so they are the same size as, or only negligibly larger than, the sample plate 24. The lower heating plate 41 is fastened directly to the work platform 1, while the upper heating plate 42 is arranged so as to project over the lower heating plate 41 at a distance that is greater than the height of the inner passive slide 9. The outer passive slide 18 can accordingly be displaced in X-Y direction between the two heating plates 41, 42, which enables the required freedom of movement for positioning the individual wells over the cover plate 35 that is recessed into the work platform 1 for the purpose of saving space in front of the incubator 5.

The cover plate 35 can also be provided next to the incubator 5. In order to keep the necessary free movement area of the passive mechanical table as small as possible in the interest of a large positioning area for the auxiliary devices and in the interest of an efficient use of the work platform 1, stationary devices in relation to which the sample plate 24 and its wells are to be positioned are advantageously concentrated within the smallest possible area.

When the inner passive slide 9 is not coupled with the pipetting head 17, i.e., in the uncoupled state of the coupling connection, it is maintained in a neutral position by means of a locking connection.

Figure 8A:
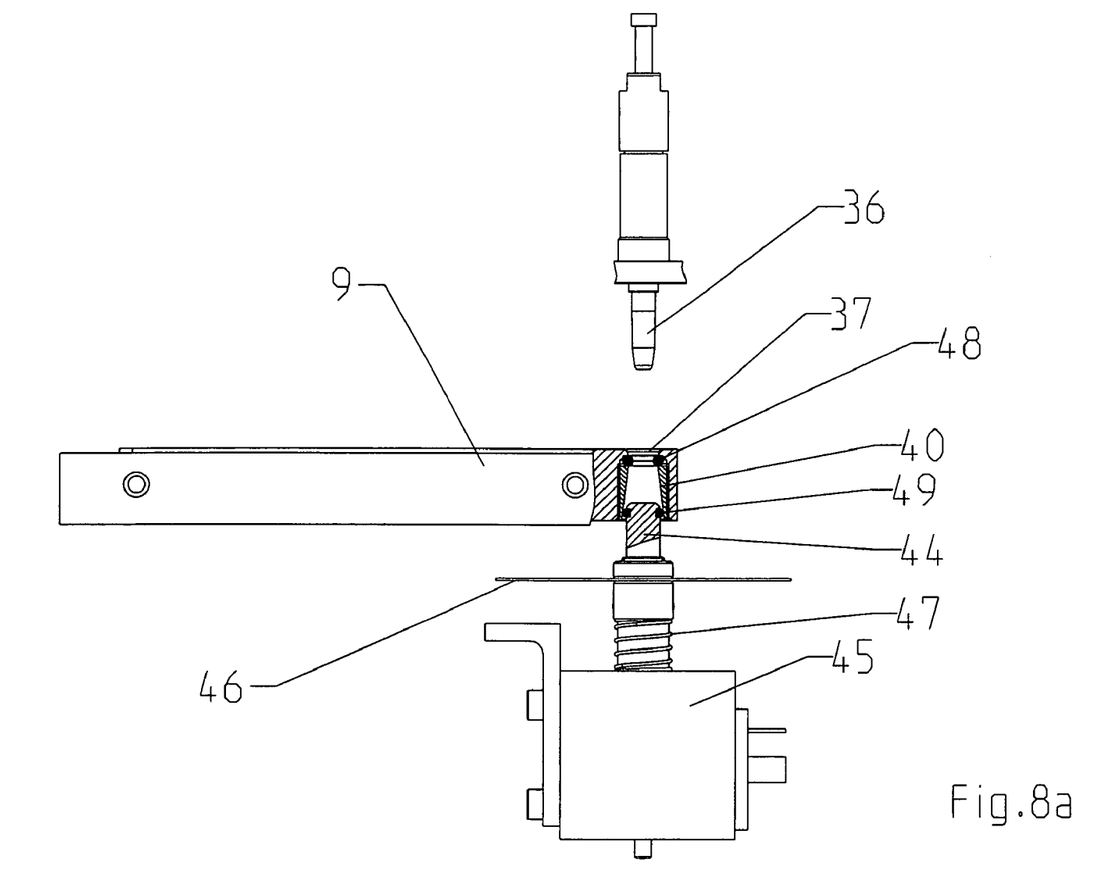
FIGS. 8a-c show the coupling connection and locking connection in a device according to FIG. 1.
Figure 8B:
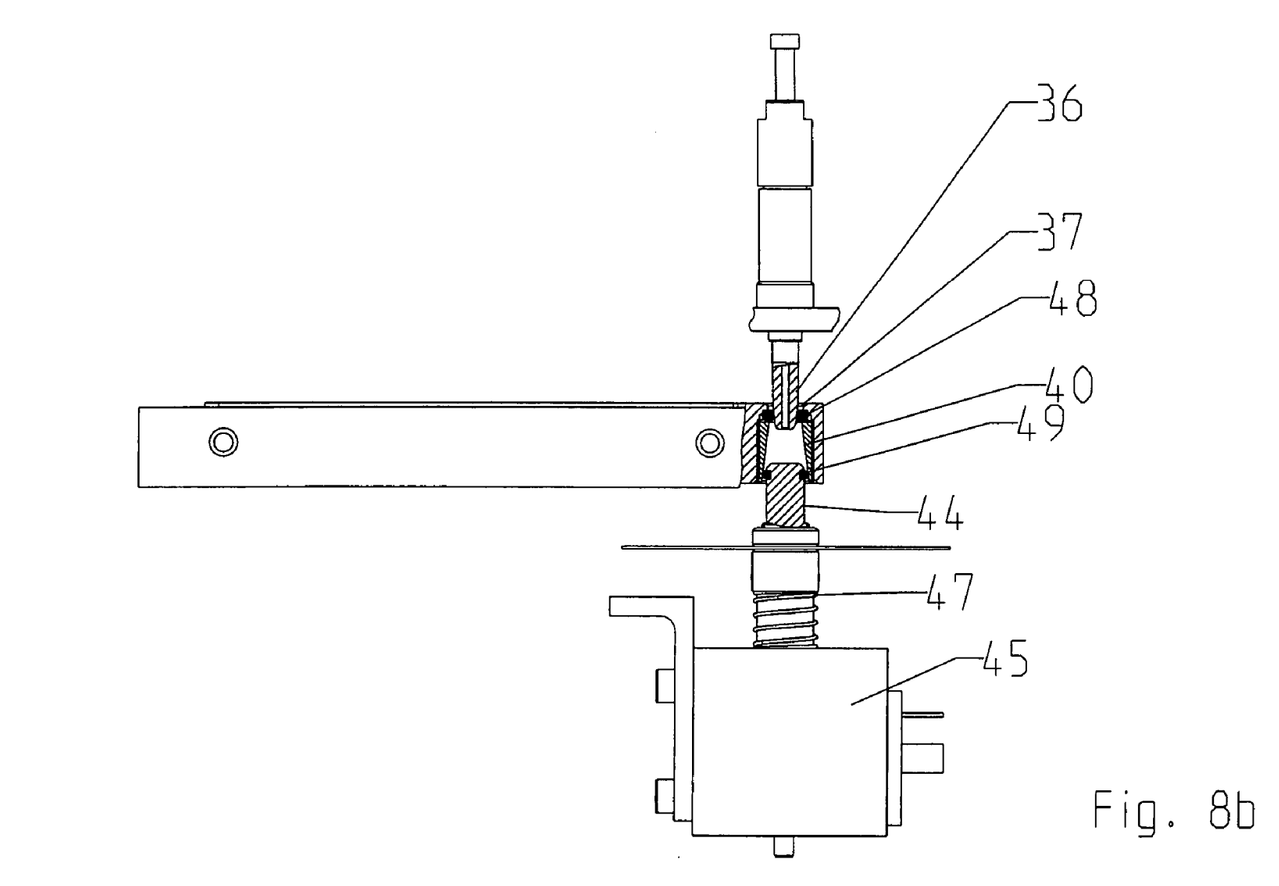
Figure 8C:
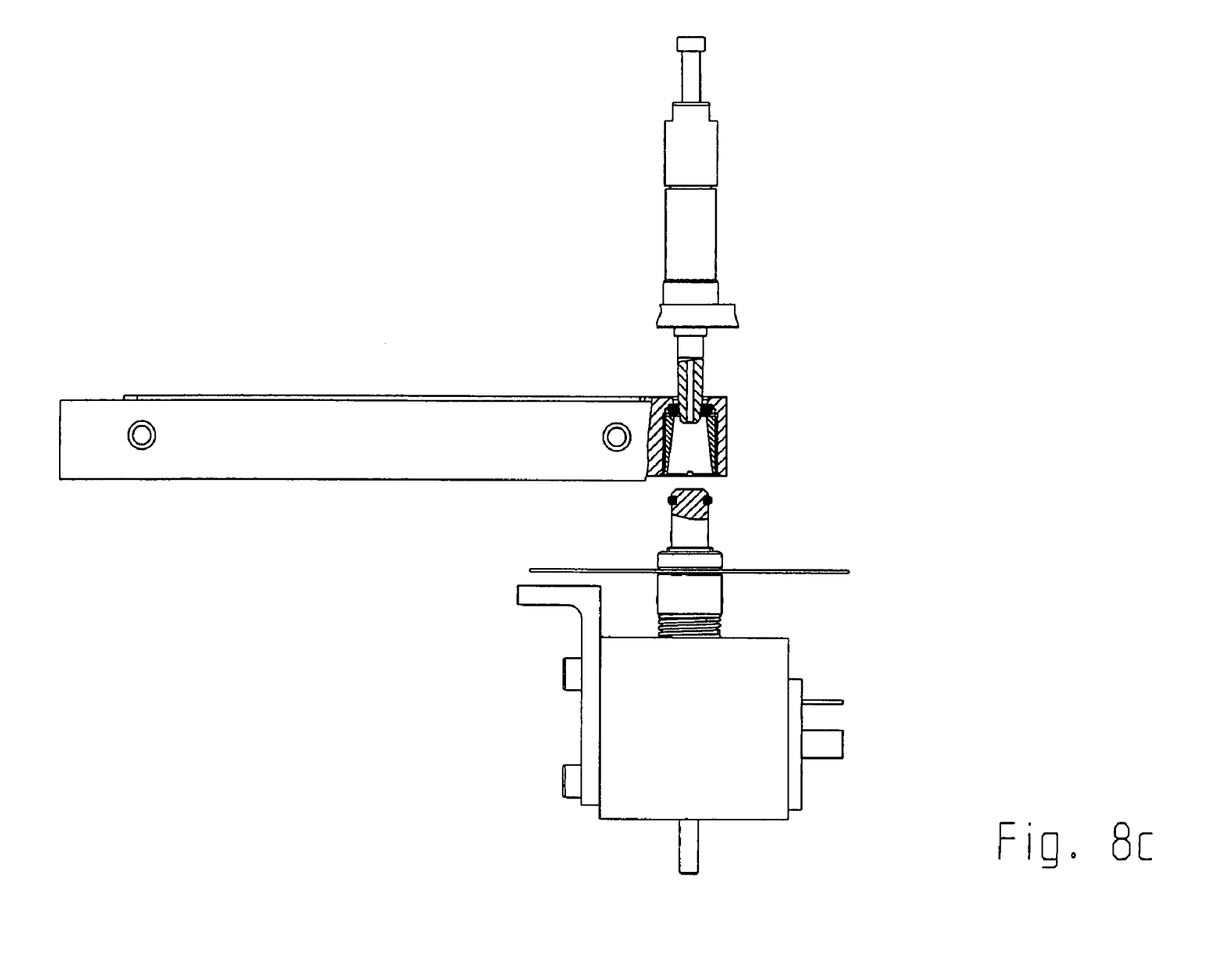
Figure 9:
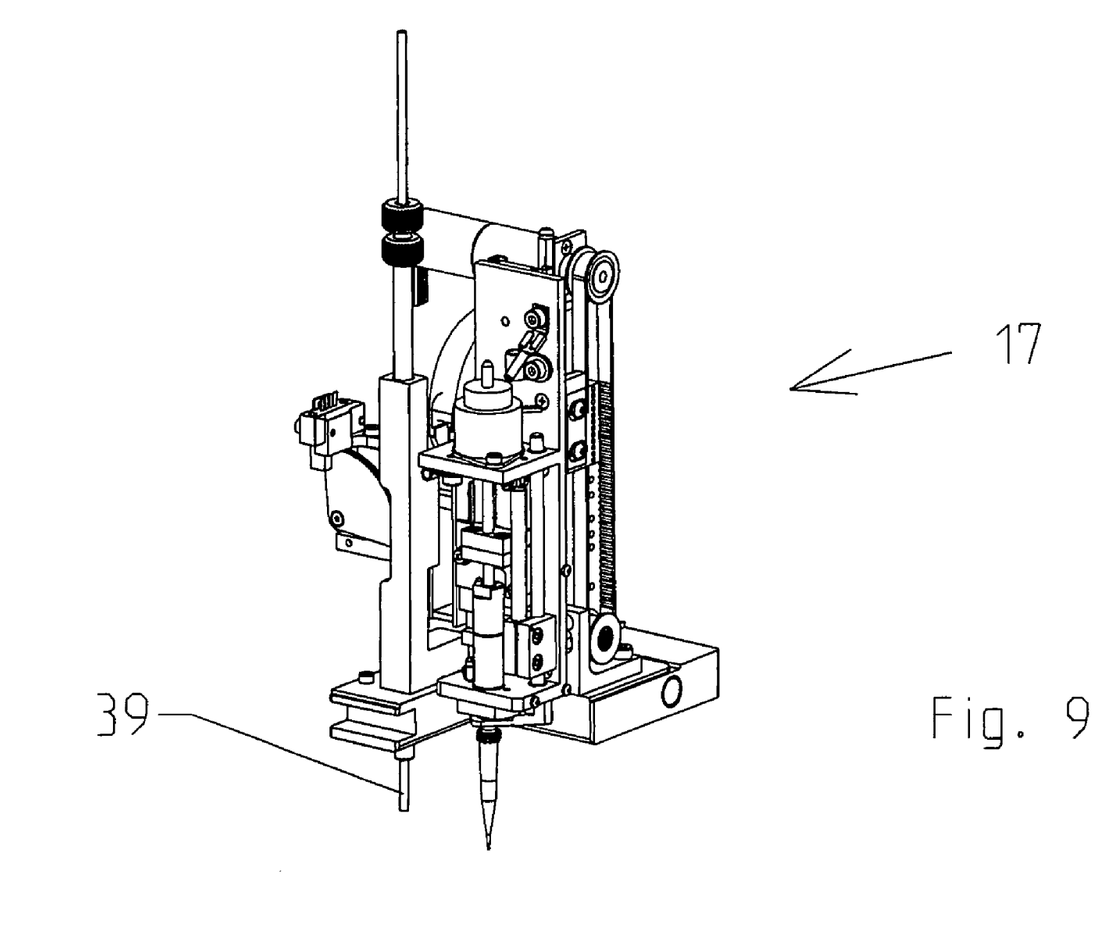
FIG. 9 shows a pipetting head without housing in a device according to FIG. 1.

FIGS. 8a-c show three different positions of the coupling connection and locking connection to illustrate the transfer of the inner passive slide 9 from the neutral position (parked position) to the inner active slide 16.

In FIG. 8a, the locking connection, as will now be described, is locked in and the coupling connection is disengaged. The inner passive slide 9, and therefore the inserted sample plate 24, remains in this position while the pipetting head 17 is moved relative to the sample plate 24 in order to prepare the samples in the wells by adding and removing liquids. By lowering the slip-on body 36 into the recess 40, the coupling connection is produced (see FIG. 8b) and the locking connection is disengaged (see FIG. 8c).

The axis of symmetry of the cutout 37 participating in the coupling connection advantageously coincides with the axis of symmetry of a recess 40 which is arranged on the opposite side of the inner passive slide 9 and which, together with the armature 44 of an electromagnet 45 mounted below the work platform 1, forms a locking connection in order to fix the inner passive slide 9 in its neutral position while the samples are being prepared. The inner passive slide 9 is held in this parked position to enable a definite transfer position from the active slide 21 or the slip-on body 36 that is provided directly on the latter.

The armature 44, which engages in the cutout 37 through an opening, not shown, in the work platform 1, is sealed relative to the work platform 1 in that it is firmly surrounded by a membrane 46 covering the opening. The membrane 46 follows the lifting movement of the armature 44 by elastic deformation.

When not supplied with current, the armature 44 is pressed into the cutout 37 by a pressure spring 47. Also, a rubber ring 49 is advantageously placed around the armature 44 in order to protect the armature 44 and the recess 40 from mechanical damage and to produce a more secure connection without play.

In particular, it is advantageous in technical respects relating to manufacture when the axes of symmetry of the cutout 37 and recess 40 coincide. The axes of symmetry can also extend parallel to one another at a fixed distance.

It was assumed in the embodiment example described above that there is one pipetting head 17 with only one pipetting channel. It will be clear to the person skilled in the art that the essence of the invention is not determined by the quantity of pipetting channels and that the head can also comprise an arrangement of a plurality of pipetting channels.

It is also only advantageous when the slip-on body or, when there are a plurality of pipetting channels at the pipetting head 17, a slip-on body for tips is used as a coupling part. Although less advantageous, it would also be possible to provide a coupling pin which is specially formed at the pipetting head 17 and which is provided only for the purpose of coupling with the inner passive slide 9. This coupling piece must be shaped in such a way that it can engage in a matching complementing piece only by movement in Z-direction. The conical shape is ideal.

Also, the locking device with an electromagnet 45 is only particularly advantageous. A purely mechanical locking connection can also carry out the same function particularly when the coupling is not formed by the slip-on body 36 which should be protected from mechanical stress in the coupling connection. For example, the locking device could be a spring-mounted shaped member which snaps into the recess 40 and is pressed out of the locking position when the coupling part engages. The locking connection could also comprise a magnet system with at least one permanent magnet.

While the foregoing description and drawings represent the present invention, it will be obvious to those skilled in the art that various changes may be made therein without departing from the true spirit and scope of the present invention.

REFERENCE NUMBERS 1 work platform
2 supply vessel
3 tip magazine
4 additional microtitration plate
5 incubator
6 positioning pin
7 adapter plate
8 tip
9 inner passive slide
10 first guide rod
11 first auxiliary rod
12 end piece
13 second auxiliary rod
14 second guide rod
15 rinsing device
16 inner active slide
17 pipetting head
18 outer passive slide
19 third guide rod
20 third auxiliary rod
21 outer active slide
22 fourth guide rod
23 fourth auxiliary rod
24 sample plate
25 end plate
26 frame plate
27 first toothed belt
28 second toothed belt
29 deflection roller
30 first motor
31 third toothed belt
32 transmission shaft
33 terminating piece
34 end part
35 cover plate
36 slip-on body
37 cutout
38 illumination device
39 suction pipe
40 recess
41 lower heating plate
42 upper heating plate
43 second motor
44 armature
45 electromagnet
46 membrane
47 pressure spring
48 O-ring
49 rubber ring

What is claimed is:

1. An automatic pipetting and analyzing device for the preparation and analysis of samples in the wells of a microtitration plate, comprising:
   a work platform on which a free movement area for the microtitration plate and positioning areas for auxiliary devices are provided for preparing the samples;
   a mechanical table which can be positioned in X-Y direction in any manner in a lower horizontal plane over the work platform and which has a holder for the microtitration plate;
   a pipetting head which can be positioned in X-Y direction in any manner in an upper horizontal plane by a drive unit and which has at least one pipetting channel with a slip-on body for tips that can be lowered in Z-direction;
   a coupling pin being provided at the pipetting head and a cutout which is shaped as the inverse of the coupling pin being provided at an inner passive slide; and
   said coupling pin and the cutout can be joined together to form a coupling connection by which a driving force acting on the pipetting head in X-Y direction is transmitted to the inner passive slide.

2. The device according to claim 1, wherein the coupling pin has a shape that is symmetric with respect to rotation.

3. The device according to claim 2, wherein the coupling pin has a conical shape.

4. The device according to claim 2, wherein the coupling pin is the slip-on body for a tip.

5. The device according to claim 4, wherein an O-ring is fitted into a recess.

6. The device according to claim 1, wherein a locking device is provided between the inner passive slide and the work platform, the inner passive slide being held in a neutral position by the locking connection.

7. The device according to claim 6, wherein the locking connection is formed by an armature of an electromagnet and a recess is formed as an inverse shape of the armature.

8. The device according to claim 7, wherein the armature has a shape that is symmetric with respect to rotation.

9. The device according to claim 6, wherein the axes of symmetry of the cutout and a recess coincide.

* * * * *